(12) United States Patent
Ellis et al.

(10) Patent No.: US 8,980,236 B2
(45) Date of Patent: Mar. 17, 2015

(54) DEPILATORY COMPOSITION

(75) Inventors: Paul Ellis, Hull (GB); Tracey Caldwell, Hull (GB)

(73) Assignee: Reckitt Benckiser (UK) Limited, Slough, Berkshire (GB)

( * ) Notice: Subject to any disclaimer, the term of this patent is extended or adjusted under 35 U.S.C. 154(b) by 209 days.

(21) Appl. No.: 12/527,354

(22) PCT Filed: Feb. 19, 2008

(86) PCT No.: PCT/GB2008/000569
§ 371 (c)(1),
(2), (4) Date: Mar. 24, 2010

(87) PCT Pub. No.: WO2008/102124
PCT Pub. Date: Aug. 28, 2008

(65) Prior Publication Data
US 2010/0330134 A1    Dec. 30, 2010

(30) Foreign Application Priority Data

Feb. 19, 2007  (GB) .................................. 0703174.3

(51) Int. Cl.
A61K 31/702   (2006.01)
A61Q 9/04     (2006.01)
A61K 8/34     (2006.01)
A61K 8/60     (2006.01)

(52) U.S. Cl.
CPC . *A61Q 9/04* (2013.01); *A61K 8/345* (2013.01); *A61K 8/60* (2013.01)
USPC ........................................................ 424/70.1

(58) Field of Classification Search
None
See application file for complete search history.

(56) References Cited

U.S. PATENT DOCUMENTS

| | | | | |
|---|---|---|---|---|
| 3,563,694 A | * | 2/1971 | Minton | 8/160 |
| 4,618,344 A | * | 10/1986 | Wells | 8/161 |
| 4,842,610 A | * | 6/1989 | Gordon et al. | 8/160 |
| 2007/0048242 A1 | * | 3/2007 | Gupta | 424/73 |

OTHER PUBLICATIONS

Jungermann (Glycerin: a key cosmetic ingredient 1991, CRC Press, chapter 13 pp. 345, 346 and 347).*
Jackson (Sugar Confectionery Manufacture 1995, Springer; p. 265).*
Simms (A Practical Guide to Beauty Therapy for Level 2, 2003, Nelson Thornes, pp. 300-301 and 311).*
Ranken Food Industries Manual 1997 springer Science & Busness Media. p. 408. 1 page.*

* cited by examiner

*Primary Examiner* — Ernst V Arnold
(74) *Attorney, Agent, or Firm* — Troutman Sanders LLP; Ryan A. Schneider; Elizabeth-Ann Weeks

(57) ABSTRACT

A depilatory composition comprising glucose syrup and a viscosity modifier comprising dextrose powder and/or crystals.

20 Claims, No Drawings

DEPILATORY COMPOSITION

BENEFIT CLAIMS

This application is a US National Stage of International Application No. PCT/GB2008/000569, filed 19 Feb. 2008, which claims the benefit of GB 0703174.3, filed 19 Feb. 2007.

FIELD OF THE INVENTION

The present invention relates to a depilatory composition and its method of use. In particular, the present invention relates to a depilatory composition comprising glucose syrup.

BACKGROUND OF THE INVENTION

Depilatory compositions containing sugars are well known. These compositions are typically formed by dissolving crystallised sugar in water at elevated temperatures. The resulting mixture is then allowed to cool to form a pliable, wax-like material. The material is typically heated, for example, in a microwave, before being applied to the skin. Strips of fabric or a non-woven material are then pressed against the treated skin to embed hairs in the depilatory composition. The strips are then pulled sharply to remove the depilatory composition and hair from the skin.

In another approach, the composition may again be heated and applied to the skin. The composition is then allowed to set or harden and then pulled sharply to remove the depilatory composition and hair from the skin without the necessity of applying a strip of fabric.

BRIEF SUMMARY OF THE INVENTION

We have now developed a depilatory composition with improved rheological properties.

According to a first aspect of the present invention, there is provided a depilatory composition comprising
  glucose syrup and
  a viscosity modifier comprising dextrose powder or crystals.

According to a second aspect, the present invention provides a method of removing hair from the skin, said method comprising
  applying a composition as described above to an area of skin,
  allowing the composition to set and hold said hair, or applying a strip of material over said composition and allowing said strip to adhere thereto, and
  removing said composition and hair by peeling said composition or said material and said composition from the skin.

DETAILED DESCRIPTION OF PREFERRED EMBODIMENTS

The depilatory composition of the present invention comprises glucose syrup in combination with a viscosity modifier comprising dextrose in crystalline and/or powder form. Without wishing to be bound by any theory, the dextrose powder is believed to be uniformly dispersed in the syrup network, improving the rheological properties of the composition. As a result, the composition provides an effective depilatory action and, at the same time, is easy to handle. For example, the depilatory composition can be applied to relatively small areas of skin to provide an effective depilatory action.

Any suitable glucose syrup may be used to produce the depilatory composition of the present invention. For example, the glucose syrup may be derived from wheat or maize, preferably wheat. The glucose syrup may have a dry solids content of 75 to 90 weight %, preferably 80 to 85 weight %, and more preferably 82.8 to 83.8 weight %. The glucose syrup may have a Dextrose Equivalent (DE) of 35 to 45, preferably 37 to 41. For the avoidance of doubt, the DE of glucose syrup is its total reducing value expressed as a percentage of the reducing value of pure dextrose and calculated on a dry weight basis.

A suitable glucose syrup may have a monosaccharide content of 75 to 85 weight %, a disaccharide content of 10 to 20 weight %, a trisaccharide content of 10 to 15 weight %. The polysaccharide content of the glucose syrup may be 45 to 65 weight %.

A suitable glucose syrup is C*Sweet 01141 sold by Cargill.

The depilatory composition of the present invention may include 60 to 90 weight % glucose syrup, preferably 80 to 85 weight % glucose syrup and most preferably 82 to 83 weight % glucose syrup. In one embodiment, the composition contains about 83 weight % glucose syrup.

The depilatory composition of the present invention includes a viscosity modifier comprising dextrose in powder or crystalline form. Preferably, dextrose powder is employed. In a preferred embodiment, the viscosity modifier consists essentially of dextrose powder. Dextrose powder is preferably employed in the absence of other sugars in crystalline form. For example, sucrose and/or fructose is/are preferably absent from the composition. In one embodiment, the depilatory composition is not formed using any disaccharides in powder or crystalline form.

The depilatory composition may contain 5 to 20 weight %, preferably 10 to 15 weight % of the viscosity modifier. The depilatory composition may contain 5 to 20 weight %, preferably 10 to 15 weight % of dextrose in powder and/or crystalline form.

The weight ratio of glucose syrup to the dextrose powder/crystals (preferably dextrose powder) in the composition may be 3:1 to 10:1, preferably 4:1 to 9:1, more preferably 5:1 to 8:1, for example 6:1 to 7:1.

The depilatory composition of the present invention may additionally include a humectant. Suitable humectants include glycerine, propylene glycol and glyceryl triacetate. Preferably, glycerine is employed. The humectant may be present in an amount of 1 to 5 weight %, preferably 2 to 4 weight %, for example, about 3 weight %.

The depilatory composition of the present invention may additionally include a moisturising active. Suitable moisturizing actives include aloe vera. Optionally, a perfume and/or a dye may also be present. Such optional ingredients may be present in an amount of 0 to 2 weight %, preferably 0 to 1 weight %, for example, 0 to 0.5 weight %.

The depilatory composition of the present invention may contain no more than 10 weight %, preferably no more than 5 weight % added water, more preferably no more than 2 weight % added water and most preferably no more than 1 weight % added water. In one embodiment, no added water is included in the composition.

Water may be added to the composition, for example, to lower the composition's viscosity. As a result, less or no heating may be required prior to applying the composition to the skin. Whilst a small amount of water is useful for lowering the viscosity of the composition, too much water should not be added as this can reduce the tackiness of the composition making it less effective for hair removal. In a preferred embodiment, the composition contains 0 to 1 weight % water, preferably 0 to 0.5 weight % water.

The depilatory composition of the present invention may have a wax-like appearance at room temperature. Accordingly, the composition may be termed a depilatory wax composition. The composition of the present invention is typically transparent and may be colourless and/or odourless. Of course, a dye may be added to the composition to provide it with a desired colour. Alternatively or additionally, a perfume may be added to provide the composition with a desired smell.

The compositions of the present invention may be prepared by any suitable method. For example the glucose syrup may be heated to an elevated temperature of, for example, 65 to 85 degrees C., preferably 70 to 80 degrees C., more preferably approximately 75 degrees C. The viscosity modifier may then be added and the mixture mixed until homogeneous. The mixture may optionally be cooled, for example, to 65 degrees C. or below, for example, to approximately 60 degrees C. If a humectant is employed, this may be added to the mixture, together with other optional components, for example, after the cooling step.

In one embodiment, the composition is packaged in a tube or container that is preferably provided with a bevelled nozzle or applicator. The tube may be less than 15 cm, preferably less than 10 cm in length. Thus, the tube may be conveniently held in the hand and used to dispense the composition onto relatively small areas of skin (e.g. eyebrows, upper lip, and chin) with accuracy.

When it is desired to be used, the composition of the present invention may optionally be warmed, for example, to a temperature of above 25 degrees C. Preferably, the composition is warmed to a temperature of 30 to 80 degrees C., more preferably 40 to 50 degrees C. Heating may be carried out by any means. For example, a user may warm a container containing the composition in his or her hands. Alternatively, the composition of the present invention may be warmed by placing a container containing the composition under a hot tap or immersing a container containing the composition in a bath of hot water. The water may be at a temperature of 30 to 80 degrees C., more preferably 40 to 50 degrees C. The length of time that the composition must be heated will depend on a number of factors, including the quantity of composition to be heated, and the nature of the container in which it is held. Suitable heating instructions may be provided in association with a container comprising the composition. An advantage of the composition of the present invention is that it can be heated to the desired temperature in a convenient manner and, desirably, maintains desirable rheological properties during use.

Once the composition has been warmed, it may be stirred, if desired, in particular to ensure a more uniform temperature throughout the composition. In a preferred embodiment, no stirring is necessary.

The composition may be applied by a user to the skin, for example, by squeezing the composition from a tube. The tube may be provided with a nozzle or applicator that is shaped (e.g. bevelled) to allow the composition to be applied directly to the skin. Alternatively, the composition may be placed in a vessel and stirred. A spatula may then be used to apply the composition.

The composition may be applied once the composition has been warmed and/or stirred, although warming and/or stirring may not always be necessary.

The composition is then allowed to set on the skin and hold the hair. Alternatively, a strip of material such as fabric, card or paper can be pressed over the composition and allowed to adhere thereto. This causes the hairs to be embedded into the composition. The composition or the material together with the composition can then be pulled or peeled from the skin in order to remove the hair from the skin. In a preferred embodiment, a strip of material such as a fabric, card or paper is applied over the composition and allowed to adhere thereto. The material together with the composition is then be pulled or peeled from the skin in order to remove the hair from the skin.

The composition is especially suitable for removing facial hair, such as hair in the eye brows, on the upper lip or chin.

An advantage of the present invention is that it can be washed off relatively easily, for example, by rinsing with water.

An embodiment of a composition according to the present invention comprises 60 to 90 weight % glucose syrup, 10 to 15 weight % dextrose powder, and 1 to 5 weight % glycerine.

The present invention will now be further described in the following Examples.

EXAMPLE 1

The depilatory wax composition shown in Table 1 below was formed by heating the glucose syrup to a temperature of approximately 75 degrees C. The powdered dextrose was then added to the glucose syrup and the mixture mixed until homogeneous. The mixture was then cooled to approximately 60 degrees C. The remaining components were then added.

The resulting composition is applied to the skin without heating. A strip of material is placed over the composition to embed hairs in the composition. The strip is then be pulled sharply to remove the composition and hair from the skin.

TABLE 1

| Material | % w/w |
| --- | --- |
| Glucose syrup | 84.8 |
| Dextrose powder | 11.5 |
| Glycerine | 3.0 |
| Water | 0.5 |
| *Aloe Vera* | 0.1 |
| Fragrance | 0.1 |
| Blue Dye | q.s. |
| Yellow Dye | q.s. |

EXAMPLE 2

The preparation method described in Example 1 was used to prepare the composition of Table 2 below. Water is not present in this composition.

The resulting composition is heated to a temperature of approximately 60 degrees C. under a hot tap. The composition is then applied to the skin. A strip of material is placed over the composition to embed hairs in the composition. The strip is then be pulled sharply to remove the composition and hair from the skin.

TABLE 2

| Material | % w/w |
| --- | --- |
| Glucose syrup | 82.3 |
| Dextrose powder | 14.5 |
| Glycerine | 3.0 |
| *Aloe Vera* | 0.1 |

TABLE 2-continued

| Material | % w/w |
|---|---|
| Fragrance | 0.1 |
| Blue Dye | q.s. |
| Yellow Dye | q.s. |

What is claimed is:

1. A depilatory composition comprising:
   glucose syrup having a monosaccharide content from 75% to 85%, a disaccharide content from 10% to 20% and a trisaccharide content from 10% to 15%; and
   a viscosity modifier comprising dextrose powder and/or crystals;
   wherein the weight ratio of glucose syrup to dextrose powder and/or crystals is 6:1 to 8:1.

2. A composition as claimed in claim 1, which comprises 60 to 90 weight % of the glucose syrup.

3. A composition as claimed in claim 2, which comprises 80 to 85 weight % of the glucose syrup.

4. A composition as claimed in claim 1, which comprises 5 to 20 weight % of the viscosity modifier.

5. A composition as claimed in claim 1, further comprising a humectant.

6. A composition as claimed in claim 5, which comprises 1 to 5 weight % of the humectant.

7. A composition as claimed in claim 5, wherein the humectant is glycerine.

8. A composition as claimed in claim 1, further comprising a moisturising active.

9. A composition as claimed in claim 1, further comprising glycerine, and wherein the composition comprises:
   60 to 90 weight % of the glucose syrup,
   10 to 15 weight % of the dextrose powder, and
   1 to 5 weight % of the glycerine.

10. A composition as claimed in claim 1, which comprises no more than 5 weight % of added water.

11. A composition as claimed in claim 1, further comprising a perfume.

12. A composition as claimed in claim 1, further comprising a dye.

13. A composition as claimed in claim 1, wherein the weight ratio of glucose syrup to dextrose powder and/or crystals is 6:1 to 7:1.

14. A method of removing hair from the skin, said method comprising:
    applying a composition as claimed in claim 1 to an area of skin,
    allowing the composition to set and hold said hair, and
    removing said composition and hair by peeling said composition from the skin.

15. A method as claimed in claim 14, which is a method for removing facial hair.

16. A method as claimed in claimed in claim 14, further comprising heating the composition to a temperature of above 25 degrees before applying the composition to the skin.

17. A method as claimed in claim 14, further comprising:
    applying a strip of material over the composition; and
    allowing the strip of material to adhere to the composition,
    wherein removing the composition and hair from the skin comprises peeling the strip of material from the skin.

18. A device for removing hair from mammalian skin comprising:
    a container provided with a bevelled nozzle or applicator, and a composition according to claim 1, wherein the container contains the composition.

19. A device according to claim 18, wherein the container is less than 15 cm in length.

20. A depilatory composition consisting of:
    glucose syrup having a monosaccharide content from 75% to 85%, a disaccharide content from 10% to 20% and a trisaccharide content from 10% to 15%; and
    a viscosity modifier comprising dextrose powder and/or crystals;
    wherein the weight ratio of glucose syrup to dextrose powder and/or crystals is 3:1 to 10:1.

* * * * *

UNITED STATES PATENT AND TRADEMARK OFFICE
CERTIFICATE OF CORRECTION

PATENT NO. : 8,980,236 B2  
APPLICATION NO. : 12/527354  
DATED : March 17, 2015  
INVENTOR(S) : Paul Ellis et al.

Page 1 of 1

It is certified that error appears in the above-identified patent and that said Letters Patent is hereby corrected as shown below:

On The Title Page, Item (73) Assignee
"Reckitt Benckiser (UK) Limited" should read -Reckitt & Colman (Overseas) Limited-.

Signed and Sealed this
Fifth Day of April, 2016

Michelle K. Lee
*Director of the United States Patent and Trademark Office*